United States Patent
Keeney et al.

(10) Patent No.: US 9,682,035 B2
(45) Date of Patent: Jun. 20, 2017

(54) INJECTABLE HYDROGEL SYSTEM TO MODULATE HOST RESPONSE AT BONE IMPLANT INTERFACE

(71) Applicant: The Board of Trustees of the Leland Stanford Junior University, Palo Alto, CA (US)

(72) Inventors: Michael Gerard Keeney, Palo Alto, CA (US); Fan Yang, Stanford, CA (US); Stuart Barry Goodman, Los Altos, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 13 days.

(21) Appl. No.: 14/378,945

(22) PCT Filed: Feb. 15, 2013

(86) PCT No.: PCT/US2013/026506
§ 371 (c)(1),
(2) Date: Aug. 14, 2014

(87) PCT Pub. No.: WO2013/126294
PCT Pub. Date: Aug. 29, 2013

(65) Prior Publication Data
US 2015/0024051 A1 Jan. 22, 2015

Related U.S. Application Data

(60) Provisional application No. 61/602,477, filed on Feb. 23, 2012.

(51) Int. Cl.
| | | |
|---|---|---|
| A61K 9/00 | (2006.01) | |
| A61L 27/52 | (2006.01) | |
| A61L 27/58 | (2006.01) | |
| A61F 2/46 | (2006.01) | |
| A61L 27/54 | (2006.01) | |
| A61K 9/06 | (2006.01) | |
| A61K 9/16 | (2006.01) | |
| A61K 38/18 | (2006.01) | |
| A61K 38/19 | (2006.01) | |
| A61K 47/10 | (2017.01) | |
| C12N 15/11 | (2006.01) | |
| A61F 2/30 | (2006.01) | |

(52) U.S. Cl.
CPC .......... *A61K 9/0024* (2013.01); *A61F 2/4675* (2013.01); *A61K 9/06* (2013.01); *A61K 9/16* (2013.01); *A61K 38/1825* (2013.01); *A61K 38/1858* (2013.01); *A61K 38/1866* (2013.01); *A61K 38/1875* (2013.01); *A61K 38/19* (2013.01); *A61K 47/10* (2013.01); *A61L 27/52* (2013.01); *A61L 27/54* (2013.01); *A61L 27/58* (2013.01); *C12N 15/11* (2013.01); *A61F 2002/30075* (2013.01); *A61F 2002/30677* (2013.01); *A61F 2002/4676* (2013.01); *A61L 2300/412* (2013.01); *A61L 2400/06* (2013.01); *A61L 2430/02* (2013.01)

(58) Field of Classification Search
CPC .............. A61F 2/4675; A61K 38/1825; A61K 38/1858; A61K 38/1866; A61K 38/1875; A61K 38/19; A61K 47/10; A61K 9/0024; A61K 9/06; A61K 9/16; A61L 2300/412; A61L 2400/06; A61L 2430/02
See application file for complete search history.

(56) References Cited

U.S. PATENT DOCUMENTS

| | | | |
|---|---|---|---|
| 5,645,592 A | | 7/1997 | Nicolais et al. |
| 6,589,549 B2 * | | 7/2003 | Shih ............... A61K 9/0024 424/426 |
| 7,884,185 B2 | | 2/2011 | Schneider et al. |
| 8,334,044 B2 | | 12/2012 | Myung et al. |
| 8,940,311 B2 * | | 1/2015 | Lim .............................. 424/400 |
| 2003/0099682 A1 * | | 5/2003 | Moussy ............... A61B 5/0031 424/423 |
| 2004/0133275 A1 | | 7/2004 | Mansmann |
| 2006/0106392 A1 | | 5/2006 | Embry |
| 2006/0188583 A1 * | | 8/2006 | Lim ............... A61K 9/0024 424/490 |
| 2008/0241214 A1 | | 10/2008 | Myung et al. |
| 2009/0112315 A1 | | 4/2009 | Fang et al. |
| 2009/0240337 A1 | | 9/2009 | Myung et al. |
| 2010/0015197 A1 | | 1/2010 | Rapaport |
| 2011/0224791 A1 | | 9/2011 | Hodorek et al. |

OTHER PUBLICATIONS

Keeney et al. Mutant MCP-1 Protein Delivery from Layer-by-Layer Coatings on Orthopaedic Implants to Modulate Inflammatory Response. Biomaterials. Dec. 2013 ; 34(38): 10287-10295.*
Anderson et al., "Biodegradation and biocompatibility of PLA and PLGA microspheres," Advanced Drug Delivery Reviews, 28, 1997, pp. 5-24.
Ayman Karkar, "Modulation of Renal Inflammation: Therapeutic Strategies," Saudi J Kidney Dis Transpl 2008; 19(1), pp. 1-19.
Logeart-Avramoglou et al., "Engineering bone: challenges and obstacles," J. Cell. Mol. Med., vol. 9, No. 1, 2005, pp. 72-84.
Morais et al., "Biomaterials/Tissue Interaction: Possible Solutions to Overcome foreign Body Response," The AAPS Journal, vol. 12, No. 2, Jun. 2010, pp. 188-196.

(Continued)

*Primary Examiner* — Robert A Wax
*Assistant Examiner* — Olga V Tcherkasskaya
(74) *Attorney, Agent, or Firm* — Beyer Law Group LLP

(57) ABSTRACT

A bone implant primer is provided. A biodegradable hydrogel component is provided. A plurality of biomolecule release depots are dispersed within the biodegradable hydrogel component wherein the plurality of biomolecule release depots comprise biomolecules for aiding implant osseointegration or biomolecules for mitigation of foreign body response. Different biomolecules may be released by the microspheres at different times.

8 Claims, 4 Drawing Sheets

(56) References Cited

OTHER PUBLICATIONS

Yasuhiko Tabata, "The importance of drug delivery systems in tissue engineering," PSTT, vol. 3, No. 3, Mar. 2000, pp. 80-89.
International Search Report and Written Opinion dated Jun. 3, 2013 from International Application No. PCT/US2013/026506.
Netti et al., "Hydrogels as an interface between bone and an implant" Biomaterials 1993. vol. 14 No. 14, pp. 1098-1104.
Sivakumar et al., "Synthesis, Characterization, and In Vitro Release of Ibuprofen from Poly (MMA-HEMA) Copolymeric Core-Shell Hydrogel Microspheres for Biomedical Applications" Journal of Applied Polymer Science, vol. 83, pp. 3045-3054 (2002).
Zhang et al, "A Dominant Negative Inhibitor Indicates that Monocyte Chemoattractant Protein 1 Functions as a Dimer", Molecular and Cellular Biology, Sep. 1995, vol. 15, No. 9, pp. 4851-4855.
Ni et al, "New Anti-Monocyte Chemoattractant Protein-1 Gene Therapy Attenuates Atherosclerosis in Apolipoprotein E-Knockout Mice" http://circ.ahajournals.org, 2001, pp. 2096-2101.
Zhang et al, "Structure/Activity Analysis of Human Monocyte Chemoattractant Protein-1 (MCP-1) by Mutagenesis: Identification of a Mutated Protein that Inhibits MCP-1 Mediated Monocyte Chemotaxis", The Journal of Biological Chemistry, 1994, vol. 269, No. 22, pp. 15918-15924.

\* cited by examiner

INJECTABLE HYDROGEL SYSTEM TO MODULATE HOST RESPONSE AT BONE IMPLANT INTERFACE

CROSS REFERENCE TO RELATED APPLICATIONS

This application claims priority under 35 U.S.C. §119(e) from U.S. Provisional Application No. 61/602,477, entitled "INJECTABLE HYDROGEL SYSTEM TO MODULATE HOST RESPONSE AT BONE IMPLANT INTERFACE", filed Feb. 23, 2012, by Michael Keeney et al. and which is incorporated by reference for all purposes.

BACKGROUND OF THE INVENTION

This invention relates generally to bone implants. US Patent Application 2009/0112315, by Z Fang et al. entitled, "MEDICAL IMPLANTS AND METHODS FOR DELIVERING BIOLOGICALLY ACTIVE AGENTS," published Apr. 30, 2009 describes implants with biologically active agents. US Patent Application 2010/0015197, by Hanna Rapaport entitled, "AMPHIPHILIC PEPTIDES AND HYDROGEL MATRICES THEREOF FOR BONE REPAIR," published Jan. 21, 2010 describes amphiphilic peptides and peptide matrices useful for biomineralization and inducing bone repair. U.S. Pat. No. 5,645,592, by Luigi Nicolais et al. entitled "USE OF HYDROGELS TO FIX BONE REPLACEMENTS," issued Jul. 8, 1997, describes the use of hydrogel coated implants. The references are incorporated by reference for all purposes.

SUMMARY OF THE INVENTION

In accordance with the invention a bone implant primer is provided. A biodegradable hydrogel component is provided. A plurality of biomolecule release depots are dispersed within the biodegradable hydrogel component wherein the plurality of biomolecule release depots comprise biomolecules for aiding implant osseointegration or biomolecules for mitigation of foreign body response.

In another manifestation of the invention an implant primer system is provided. An applicator is provided. A liquid biodegradable hydrogel component is dispensed by the applicator, wherein the liquid biodegradable hydrogel component solidifies when dispensed by the applicator, and wherein the applicator is adapted to dispense the liquid biodegradable hydrogel component into a bone cavity into which an implant is placed. A plurality of biomolecule release depots are within the liquid biodegradable hydrogel component.

In another manifestation of the invention a method for inserting a bone implant into a bone is provided. A cavity is formed in the bone. A liquid biodegradable hydrogel is applied on a surface of the cavity, wherein the liquid biodegradable hydrogel comprises a plurality of biomolecule release depots. The bone implant is placed into the cavity.

The invention and objects and features thereof will be more readily apparent from the following detailed description and appended claims when taken with the drawings.

DETAILED DESCRIPTION OF ILLUSTRATED EMBODIMENTS

The present invention will now be described in detail with reference to a few preferred embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to not unnecessarily obscure the present invention.

Over 1 million total joint replacements are performed every year in the United States alone, and these numbers are increasing due to our aging population and the fact that total joint replacement (TJR) is being performed in younger patients. TJR is a highly successful procedure, however the long-term survivorship, especially in younger, more active patients, is limited by wear of the bearing surfaces. Wear begins during the initial edding inphase and continues during use of the TJR. Wear particles stimulate chronic inflammation that leads to peri-prosthetic bone loss and implant loosening. The hospital costs for the revision procedures alone exceeded $3 billion per year. Embodiments of the invention provide a novel biomolecule delivery system that, when injected at the bone implant interface, delivers biologics in a sequential manner to reduce wear-particle initiated inflammation while promoting faster integration with the host bone tissue. Various embodiments are very flexible and may be combined with a broad range of commercially available TJR implants for improved clinical outcome and decreased incidences of implant failure and joint revision surgery.

Figure 1:
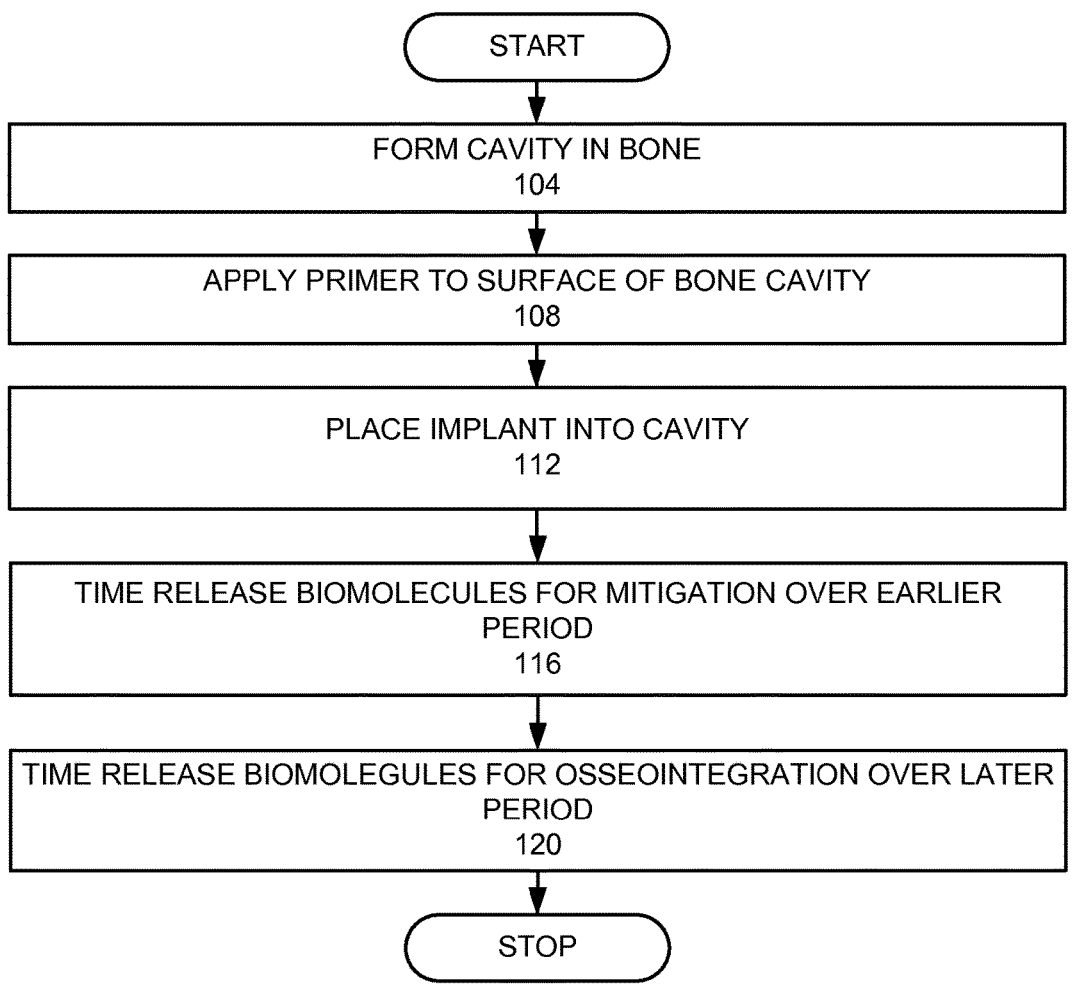
FIG. 1 is a high level flow chart of an embodiment of the invention.

FIG. 1 is a high level flow chart of an embodiment of the invention. A cavity is formed in a bone (step 104). A primer is applied to the surface of the bone cavity (step 108). An implant is placed into the cavity (step 112). Biomolecules for mitigation of foreign body response are released over an earlier time period (step 116). Biomolecules for osseointegration are released over a later time period (step 120).

EXAMPLE

Figure 2:
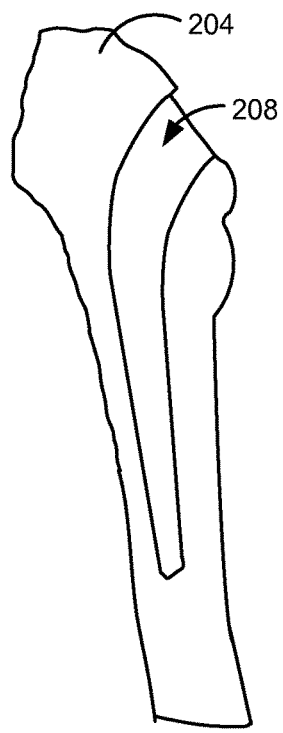
FIGS. 2A-C are cross-sectional schematic views of part of a bone in an embodiment of the invention.
Figure 2:
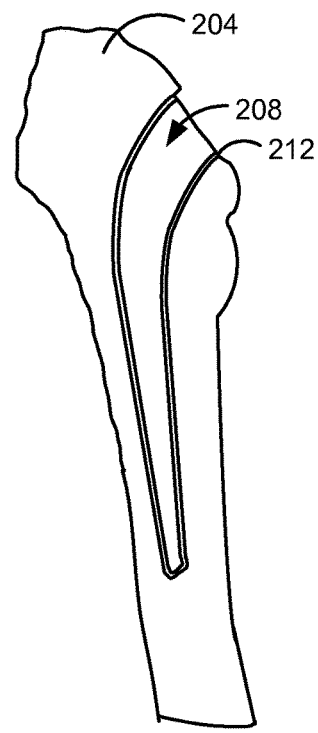
Figure 2:
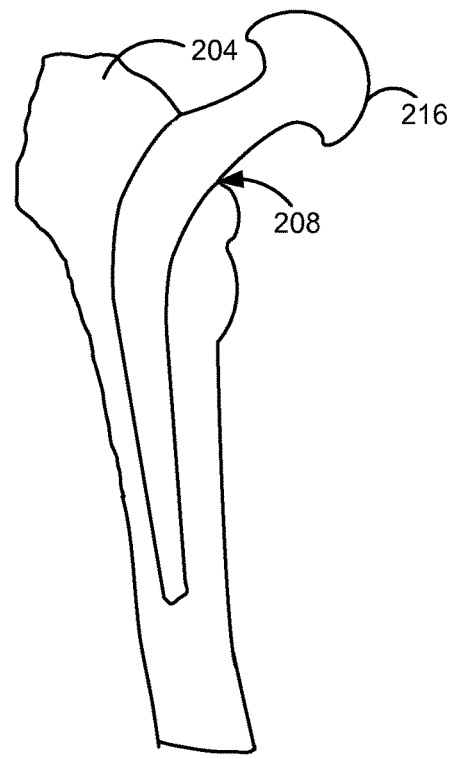

In an example, a cavity is formed in a bone (step 104). FIG. 2A is a cross-sectional schematic view of part of a bone 204 in which a cavity 208 has been formed. The bone 204 may be part of a femur or some other bone. For a femur, the femur may be reamed to form the cavity 208. In the alternative, the cavity 208 may be the result of a previous total joint replacement procedure. In other embodiments of the invention, a cavity does not need to be made in a bone.

A primer is applied to the surface of the bone cavity (step 108). FIG. 2B is a cross-sectional schematic view of part of the bone 204 after a primer 212 is applied to the surface of the bone cavity 208. The primer 212 may be absorbed into a porous surface of the bone cavity 208, but is shown as a layer so that the primer 212 may be clearly indicated.

Figure 3:
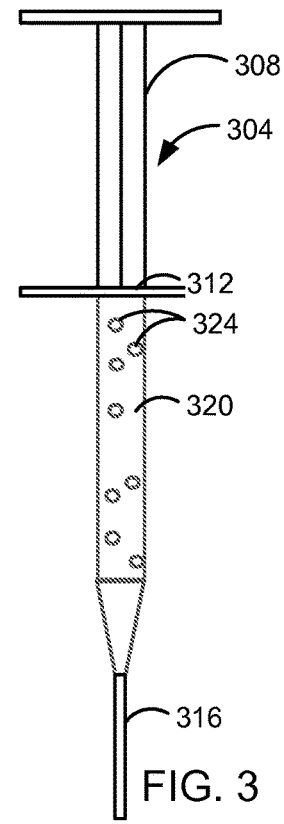
FIG. 3 is a schematic view of an applicator in the form of a syringe in an embodiment of the invention.

Various methods may be used with different devices and primers in different embodiments for applying the primer 212. FIG. 3 is a schematic view of an applicator in the form of a syringe 304, comprising a plunger 308 and a barrel 312. The syringe 304 may also have a nozzle 316. The barrel 312 of the syringe 304 contains the primer. In this embodiment, the nozzle 316 allows the application of the primer into the surface of a cavity that is greater than 250 cm deep and less than 7 cm wide.

The primer comprises a biodegradable hydrogel component 320 and a plurality of biomolecule release depots dispersed within the biodegradable hydrogel component 320. The plurality of biomolecule release drug depots have a plurality of biomolecule release drug depots with biomolecules for aiding implant osseointegration and a plurality of biomolecule release drug depots with biomolecules for mitigation of foreign body response. In this embodiment, the biomolecule release drug depots are in the form of microspheres 324.

An implant is inserted into the cavity (step 112). FIG. 2C is a cross-sectional schematic view of part of the bone 204 after an implant 216 is inserted into the bone cavity 208.

Biomolecules for mitigation of foreign body response are released over an earlier time period (step 116). Biomolecules may be drugs, growth factor, DNA, genes and other molecules that modulate the host environment. Biomolecules for mitigation of foreign body response may be 7-ND, which are biomolecules for mitigating foreign body response, receptor antagonist, such as mutants of macrophage chemoattractant protein-1 (MCP-1) and other anti-inflammatories, bactericidal agents, and antibiotics. Biomolecules for osseointegration are released over a later time period (step 120). Biomolecules for osseointegration may be bone morphogenetic protein 2 (BMP-2), bone morphogenetic protein 7 (BMP-7), vascular endothelial growth factor (VEGF), platelet-derived growth factor (PDGF), and fibroblast-derived growth factor (FGF).

Figure 4:
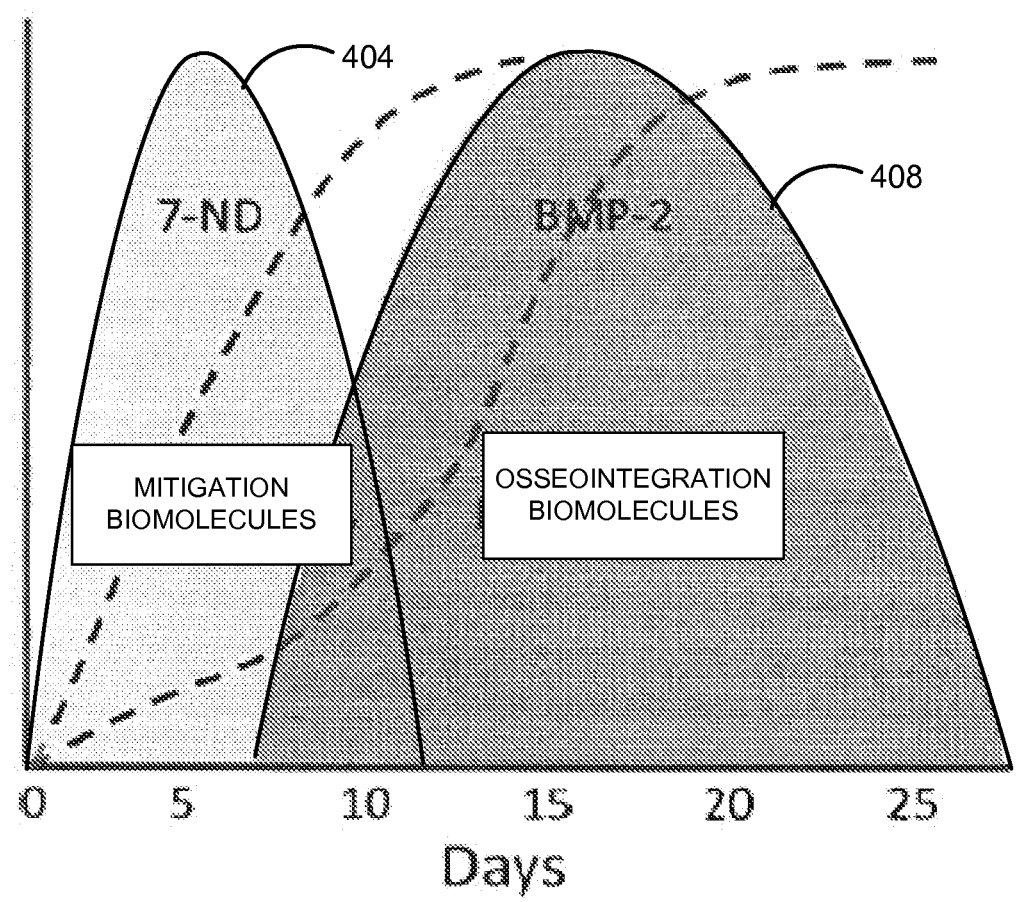
FIG. 4 is a graph of a release of biomolecules for mitigation of foreign body response and biomolecules for osseointegration according to an embodiment of the invention.

FIG. 4 is a graph of a release of biomolecules for mitigation of foreign body response and biomolecules for osseointegration according to an embodiment of the invention. In this embodiment, the microspheres 324 with biomolecules for mitigation of foreign body response provide a time release of the biomolecules for mitigation of foreign body response over a period from day 0 to day 12, with a peak concentration at about day 5, as shown in FIG. 4. As a result, biomolecules for mitigation of foreign body response are provided within two weeks of the application and solidification of the biodegradable hydrogel, so that biomolecules for mitigation of foreign body response are not released after two weeks after application, as shown by curve 404. The microspheres 324 for osseointegration provide a time release of the biomolecules for osseointegration over a period from day 7 to day 28, with a peak concentration at about day 16, as shown by curve 408. In this example, the peak concentration for the biomolecules for mitigation of foreign body response is before the peak concentration for the biomolecules for osseointegration, thus the release for the biomolecules for mitigation of foreign body response is over an earlier time period, and the release for the biomolecules for osseointegration is over a later time period. In addition, in this example, the beginning of the release of the biomolecules for mitigation of foreign body response is before the beginning of the biomolecules for osseointegration, thus the release for the biomolecules for mitigation of foreign body response is over an earlier time period, and the release for the biomolecules for osseointegration is over a later time period. In addition, in this example, the termination of the release of the biomolecules for mitigation of foreign body response is before the termination of the biomolecules for osseointegration, thus the release for the biomolecules for mitigation of foreign body response is over an earlier time period, and the release for the biomolecules for osseointegration is over a later time period. In this particular application, the anti-inflammatory protein would be designed to reduce inflammation surrounding the implant while simultaneously enhancing fixation. The biodegradable hydrogel will form the bone-implant interface and crosslink in situ.

This embodiment of the invention first provides biomolecules for mitigation of foreign body response, to reduce foreign body response caused by the implant. Once the foreign body response caused by the implant is mitigated, the biomolecules for osseointegration are provided to cause the bone to become integrated with the implant. Other biomolecules may be added at other times, controlled by the release depots in order to enhance blood vessel formation, recruit cells to the site, enhance cell proliferation, or encourage bone formation. The release of mitigation biomolecules before osseointegration biomolecules would help to reduce the risk of osteolysis at the bone implant interface. Osteolysis may hinder implant integration and lead to implant loosening. By mitigating foreign body response first, an environment is created in which new bone formation can flourish. However, some embodiments of the invention may not provide mitigation biomolecules before providing osseointegration biomolecules. In other embodiments, the mitigation biomolecules would be released concurrently with the osseointegration biomolecules.

In this embodiment, the biodegradable hydrogel component 320 comprises a polyethyleneglycol (PEG) based hydrogel.

In this embodiment, the microspheres 324 for biomolecules for mitigation of foreign body response and the microspheres 324 for biomolecules for osseointegration may be made of polyglycolic acid (PGA), polylactic acid (PLA), poly(lactic-co-glycolic) acid (PLGA), or polycaprolactone (PCL). Different parameters, such as size or material may be used to control release time.

In other embodiments of the invention, other applicators may be used. Such applicators may be brushes, aerosol spray systems, or other application devices. For applying the primer on a surface in a deep cavity more than 250 cm long, a brush would need to be long and thin, such as a thin bottle brush type brush. Other application systems would use a nozzle to evenly apply primer on a surface in a deep cavity. Other embodiments may apply the primer to a flat bone surface, instead of in a cavity.

Embodiments of the invention use microspheres 304 as the biomolecule release depots, therefore multiple biomolecules may be loaded in separate microspheres. As microsphere release rate can be controlled during fabrication (through material choice), the rate of biomolecule release can be independently controlled. The system is also injectable and crosslinks in-situ. When designed in this manner, the reservoir system can be applied directly to the bony surface. The converse of this is applying the coating to the implant surface which is technically challenging, expensive and can be easily removed during implant placement.

In other embodiments, only biomolecules for mitigation of foreign body response or biomolecules for osseointegration, but not both, are provided. In other embodiments, biomolecules for mitigation of foreign body response, biomolecules for osseointegration, biomolecules for cell recruitment, biomolecules for cell proliferation, and biomolecules for angiogenesis or vascularization are all provided over different time periods.

The hydrogel based system may also be used as a treatment to restabilize a loosened implant. The biodegradable hydrogel would be injected into the peri-prosthetic space to deliver biomolecules designed to restabilize the joint.

The biodegradable hydrogel can be applied to the bony surface prior to implant placement. When the implant is inserted the biodegradable hydrogel will reside at the bone-implant interface and crosslink link itself. The microspheres will then deliver biomolecules at a rate pre-determined during fabrication. An injectable gel avoids the need to coat the implant surface. By using microspheres as biomolecule delivery reservoirs, it is possible to deliver multiple biomolecules with independently controlled release kinetics. Applying the primer on the bone just before placing the implant allows for the biodegradable hydrogel to cement the implant and to support the microspheres. Before application, the primer may be refrigerated or store in a way that maintains the biomolecules and microspheres.

Embodiments of the invention are advantageous over surface treatments of joint implants by developing a coating for implant surface itself by treating the host bone tissue by applying a primer to the host bone. Coatings on implant surfaces are easily removed during implant placement.

Figure 5:
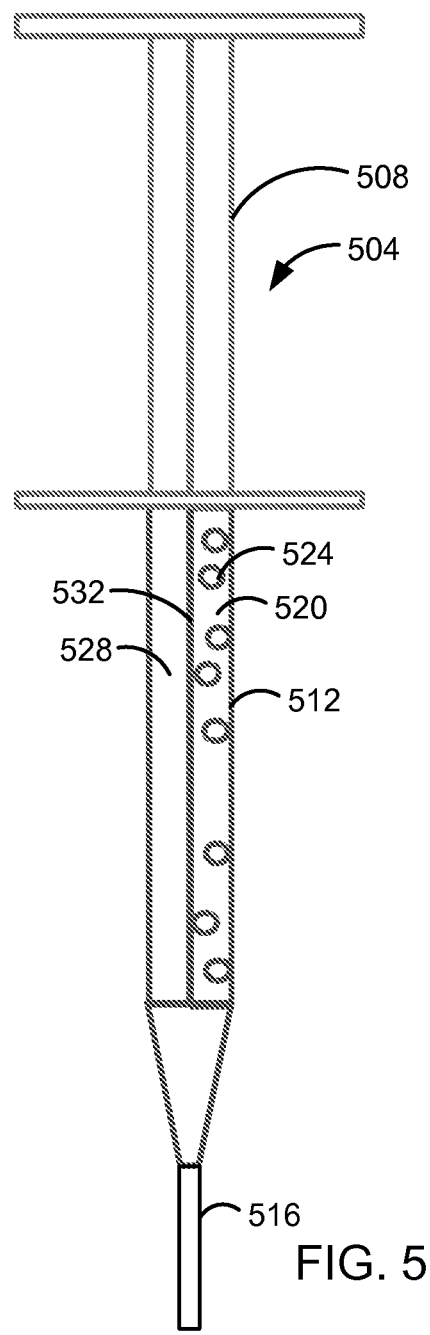
FIG. 5 is a schematic view of an applicator in the form of a syringe in another embodiment of the invention.

In other embodiments of the invention, the biodegradable hydrogel component may be PEG. In another embodiment of the invention, the biodegradable hydrogel component must be combined with another biodegradable hydrogel component to form a biodegradable hydrogel. FIG. 5 is a schematic view of an applicator in the form of a syringe 504, comprising a plunger 508, a barrel 512, and a nozzle 516. Within the barrel 512 is a first chamber with the primer comprising a first biodegradable hydrogel component 520 and a plurality of microspheres 524. Within the barrel 512 is a second chamber with a second biodegradable hydrogel component 528. The first chamber is separated from the second chamber by a wall 532 within the barrel 512. When the primer and the second biodegradable hydrogel component 528 are expelled from the barrel 512 by the plunger 508, they may combine after leaving the nozzle 516, which begins a reaction to cause the first and second biodegradable hydrogel components 520, 528 to form into a biodegradable hydrogel, which is dispensed and solidifies on a bone surface. The plurality of microspheres 524 are supported the solidified biodegradable hydrogel.

In another embodiment of the invention the biodegradable hydrogel component solidifies when exposed to UV light. In other embodiments, the hydrogel may be photo-initiated by other frequencies or frequency ranges of light.

While this invention has been described in terms of several preferred embodiments, there are alterations, permutations, modifications and various substitute equivalents, which fall within the scope of this invention. It should also be noted that there are many alternative ways of implementing the methods and apparatuses of the present invention. It is therefore intended that the following appended claims be interpreted as including all such alterations, permutations, modifications, and various substitute equivalents as fall within the true spirit and scope of the present invention.

What is claimed is:

1. A bone implant primer comprising a biodegradable hydrogel component and biomolecule release depots dispersed within the biodegradable hydrogel component, and wherein a first plurality of biomolecule release depots comprises biomolecules for mitigation of foreign body response including at least one of macrophage chemoattractant protein-1 or its mutant 7-ND, and wherein a second plurality of biomolecule release depots comprises biomolecules for aiding implant osseointegration including at least one of bone morphogenetic protein 2, bone morphogenetic protein 7, vascular endothelial growth factor, platelet-derived growth factor, or fibroblast-derived growth factor, and wherein the first plurality of biomolecule release depots releases biomolecules for mitigation of foreign body response for no more than 12 days, and the second plurality of biomolecule release depots releases biomolecules for implant osseointegration for at least 16 days.

2. The bone implant primer, as recited in claim 1, wherein the biodegradable hydrogel component turns from a liquid to a solid when placed on bone.

3. The bone implant primer, as recited in claim 1, wherein the biodegradable hydrogel component remains a liquid at a temperature below body temperature and becomes a solid hydrogel at body temperature.

4. The bone implant primer, as recited in claim 1, further comprising a third plurality of biomolecule release depots including angiogenic biomolecules, vascularization biomolecules, cell recruitment biomolecules, or cell proliferation biomolecules.

5. An implant primer system comprising an applicator and a liquid biodegradable hydrogel component, wherein the liquid biodegradable hydrogel component becomes a solid hydrogel when dispensed by the applicator, and the applicator is adapted to dispense the liquid biodegradable hydrogel component into a bone cavity into which an implant is placed; and wherein the liquid biodegradable hydrogel component comprises biomolecule release depots dispersed within the liquid biodegradable hydrogel component; wherein a first plurality of biomolecule release depots comprises biomolecules for mitigation of foreign body response including at least one of macrophage chemoattractant protein-1 or its mutant 7-ND; and a second plurality of biomolecule release depots comprises biomolecules for aiding implant osseointegration including at least one of bone morphogenetic protein 2, bone morphogenetic protein 7, vascular endothelial growth factor, platelet-derived growth factor, or fibroblast-derived growth factor; and wherein the second plurality of biomolecule release depots continue to release the biomolecules for implant osseointegration for at least two weeks after the biodegradable hydrogel component becomes a solid hydrogel.

6. The implant primer system, as recited in claim 5, wherein the liquid biodegradable hydrogel component remains a liquid at a temperature below body temperature and becomes a solid hydrogel at body temperature.

7. The implant primer system, as recited in claim 5, wherein the liquid biodegradable hydrogel component comprises at least two components and wherein the applicator comprises at least two compartments, wherein at least two components of the biodegradable hydrogel are held in the applicator separately, and wherein the applicator dispenses and combines components of the biodegradable hydrogel, wherein the combining of the components of the biodegradable hydrogel cause the biodegradable hydrogel to solidify.

8. The implant primer system, as recited in claim 5, further comprising an implant for placing into the bone cavity.

\* \* \* \* \*